US00PP14762P2

(12) United States Plant Patent
Henny

(10) Patent No.: US PP14,762 P2
(45) Date of Patent: May 4, 2004

(54) DIEFFENBACHIA PLANT NAMED 'STERLING'

(50) Latin Name: *Dieffenbachia hybrida*
Varietal Denomination: Sterling

(75) Inventor: Richard J. Henny, Apopka, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 7 days.

(21) Appl. No.: 10/299,080

(22) Filed: Nov. 19, 2002

(51) Int. Cl.[7] ..... A01H 5/00

(52) U.S. Cl. ..... Plt./378
(58) Field of Search ..... Plt./378

(56) References Cited

U.S. PATENT DOCUMENTS

PP6,858 P * 6/1989 Frazer ..... Plt./88

* cited by examiner

*Primary Examiner*—Bruce R. Campell
*Assistant Examiner*—Susan B. McCormick

(57) ABSTRACT

A new and distinct Dieffenbachia hybrid with deep shiny green leaves highlighted by a bright white midrib that extends into the leaf blade along the lateral veins and down through the petioles to the main stem.

2 Drawing Sheets

1. The leaves are very deep green and are highlighted by a dramatic white midrib that extends from the leaf base to the leaf tip.
2. The midrib coloration branches into the leaf blade along the lateral veins to give a herring-bone pattern appearance.
3. The leaf midrib color extends down the entire length of the petiole to where it clasps the main stem.
4. Plants are compact and well-branched averaging 4–8 basal shoots per plant.

DESCRIPTION

The present invention comprises a new and distinct cultivar of Dieffenbachia, botanically known as *Dieffenbachia hybrida,* and referred to by the cultivar name 'Sterling'.

The new cultivar is a product of a planned breeding program carried out by the inventor Richard Henny in Apopka, Fla. Dr. Henny has performed many crosses with Dieffenbachia since 1980 as part of his extensive ornamental tropical foliage plant breeding program.

The new cultivar is a product of a cross-pollination made between Dieffenbachia 'Victory' (pollen parent; not patented) and Dieffenbachia 'Tropic Marianne' U.S. Plant Pat. No. 8,832; seed parent).

The cultivar was discovered from the progeny of the stated cross by Richard J. Henny in Apopka, Fla. It was selected because of its outstanding shiny dark green leaves that were highlighted by a bright white midrib. Sterling lacked the foliar variegation patterns present in each parent plant. Asexual propagation by cuttings, first performed by Richard J. Henny in Apopka, Fla., was used to increase the number of plants for evaluation. Subsequently, plants were propagated by tissue culture, which also has demonstrated the stability of the combination of characteristics of Sterling from generation to generation.

The following observations, measurements and values describe plants grown in Apopka, Fla., under greenhouse conditions which closely approximate those generally used in horticultural practice.

The following traits have been repeatedly observed to be characteristics, which in combination distinguish Sterling from other Dieffenbachia of the same general type, for example, the well-known cultivars such as Camille and Compacta.

1. The leaves of Sterling lack any type of foliar variegation making it unlike Camille, Compacta, and other Dieffenbachia cultivars grown commercially today.

2. The leaves are very deep green and are highlighted by a bright white midrib that extends from the leaf base to the leaf tip.

3. The midrib coloration branches into the leaf blade along the main lateral veins to give a herring-bone pattern appearance.

4. The midrib color extends from the leaf base down the entire length of the petiole, which clasps the main stem resulting in a showy stem.

5. Plants are compact and well-branched averaging 4–8 basal shoots per plant.

All color references are measured against The Royal Horticultural Society Colour Chart. Colors are approximate as color depends on horticultural practices such as light level and fertilization rate, among others, without, however any variance in genotype.

BRIEF DESCRIPTION OF THE DRAWINGS

The two color photographic drawings were taken from a typical plant of Dieffenbachia 'Sterling' grown in a 20 cm diameter pot (3.9 liter volume), approximately 24 weeks after planting a 12-week-old liner obtained by tissue culture and grown under appropriate growing conditions. Colors are as accurate as possible with color illustrations of this type.

Figure 1:
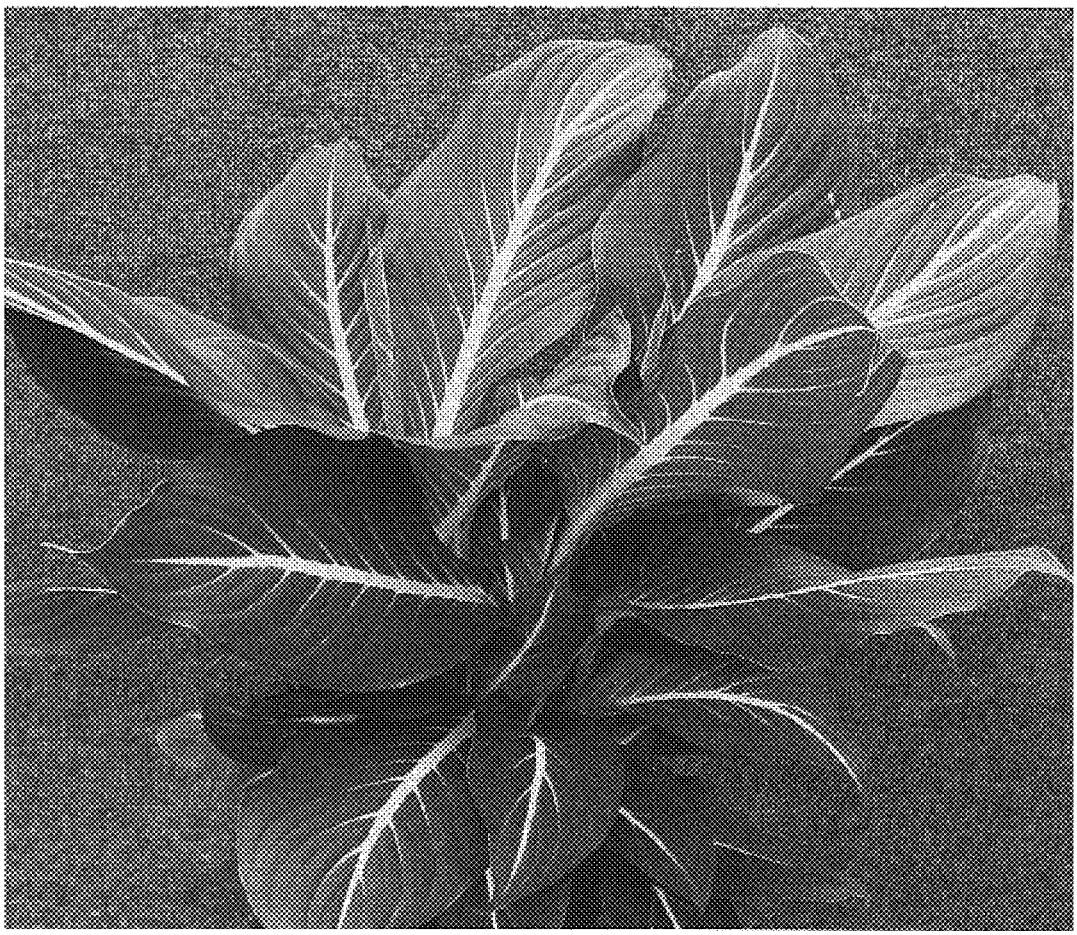
FIG. 1. The first drawing depicts a top perspective view of a plant of 'Sterling'.
Figure 2:
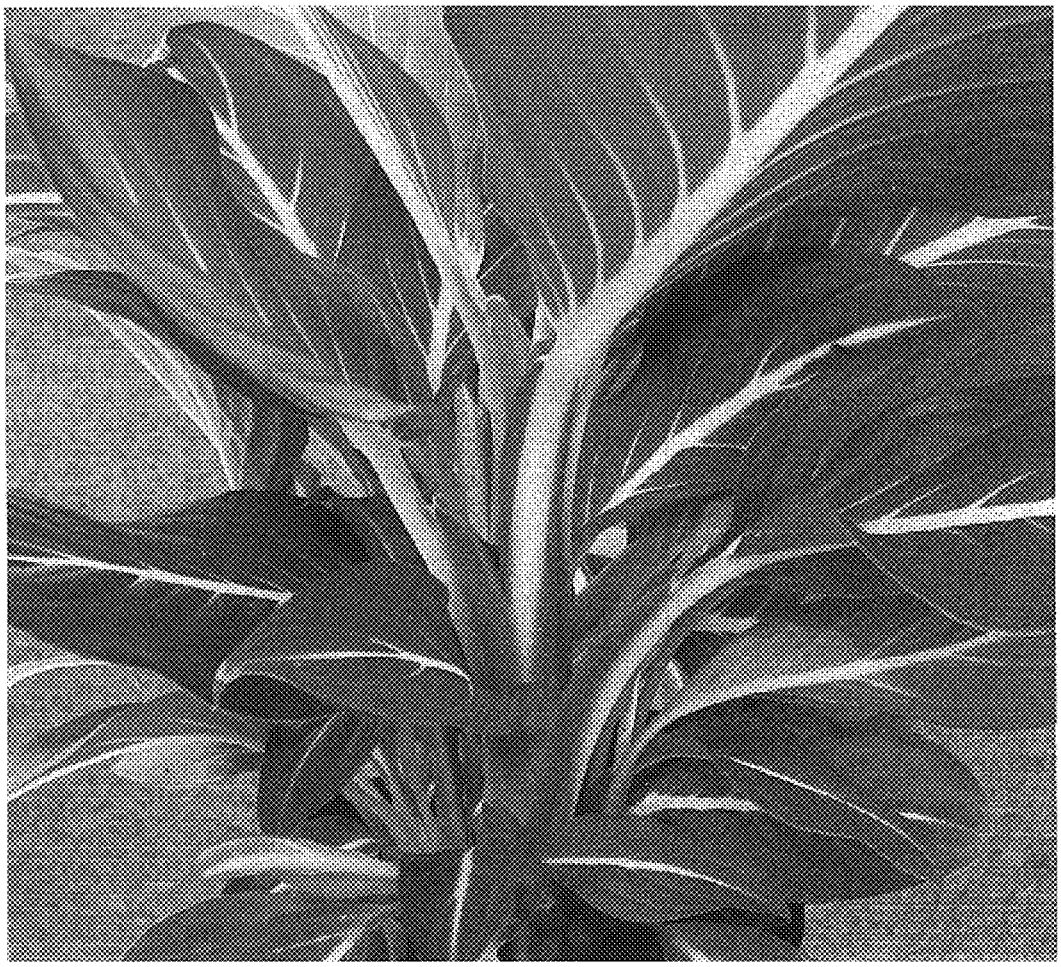
FIG. 2. The second drawing depicts the upper and lower leaf surface showing how the white midrib is visible from both perspectives and how the white leaf midrib color extends down the center of the petiole to where the petiole attaches to the main stem.

Origin: Seedling selected from a cross of Dieffenbachia 'Victory' (pollen parent; not patented) and Dieffenbachia 'Tropic Marianne' U.S. Plant Pat. No. 8,832; seed parent).

Classification:

Propagation: Asexual propagation either by tissue culture, stem cuttings or division.

Plant: In a 12 cm diameter pot for a plant grown from a 12 week old liner after 20 weeks under appropriate growing conditions, Sterling is approximately 26–30 cm from the soil surface to the junction of the petioles of the last two (2) unrolled leaves, and has canopy width of approximately 50–60 cm.

Stem:

*Growth pattern.*—The stem is erect in growth and is 2.0 to 2.5 cm in diameter five (5) cm above the soil surface. Internode distance is approximately 1.7 cm to 2.0 cm at five (5) cm above the soil.

*Color.*—The stem color is 137A. This color is visible in small irregular triangular-shaped areas between where the petioles clasp the stem. The color is uniform with no mottling.

Petiole: The following information is based on the $4^{th}$ expanded leaf from the apex.

*Dimensions.*—The petiole has fleshy edges extending from the midrib and referred to as wings. The wings are approximately 8 mm to 12 mm wide one-half the distance from the petiole base to the wing apex. The wings extend from the base of the petiole to within approximately 1 mm to 5 mm of the base of the leaf. The wings are distinctly rolled inward lengthwise where not in contact with the stem. The petiole follows the stem axis but diverges from the axis approximately 4.0 cm to 6.0 cm from the leaf base, forming a horizontal distance from the edge of the stem to the leaf base of approximately 3.2 cm to 4.0 cm. The petiole is often curved from the tip of the wings to the base of the leaf. The petiole is approximately 7 mm to 10 mm in diameter one-half the distance between the top of the wing and the base of the leaf. The petiole is approximately 10.8 cm to 12.0 cm in length.

*Color.*—The petiole and petiole wings are 137 A–B on the outer edges extending inward about ⅓ the petiole width from each edge. The center of the petiole is the same as the leaf midrib, 155D.

Leaf:

*Growth pattern.*—The leaf is oblong with a cuspidate apex and cordate base. The margin is entire. The leaf is asymmetric with the side of the leaf unrolling first having less surface area than the side unrolling last. The leaf is oriented parallel to the stem axis at the time of full unrolling, changing to approximately 40–50 degrees above perpendicular to the stem axis as more leaves unroll above it. The midrib is straight over two-thirds the length of the leaf and curved downward toward the tip. The leaf blade is somewhat wavy from the midrib to the margin. The leaf blades are angled upward from the midrib but flatten as the leaf ages.

*Dimensions.*—For the pot size and growing time indicated, the largest leaf is approximately 36–38 cm long and approximately 15–16 cm wide. An average sized leaf is approximately 35–36 cm long and approximately 14–15 cm wide. The leaf is moderately thick and somewhat puckered.

*Midrib.*—The leaf midrib is thick and prominent and ranges from a width of 1 cm at the base of the leaf to approximately 0.7 to 0.8 cm at a distance equally between the leaf base and the leaf tip. The adaxial and abaxial leaf midrib color is the same 155D.

*Primary veins.*—The primary veins are sunken into the adaxial surface and protrude from the abaxial surface. The primary veins are the same color 155D as the leaf midrib. This color blends to green 137A approximately one third to one half the way to the leaf margin.

*Color and pattern.*—Leaf color pattern is uniform. Mature leaf blades are 137A on the adaxial surface and 137D on the abaxial surface. Newly opened leaves are somewhat lighter than older leaves but darken to the normal color 137A within a few days.

*Axillary breaks.*—In our experimental growth tests plants produced approximately 4–8 axillary breaks with at least one leaf expanded.

*Inflorescence.*—Typical of Dieffenbachia and does not have commercial significance. The spathe is a uniform 146B/C. The terminal male flowers are orange-white 159A/B and cover approximately the upper ½ of the spadix. Female flowers cover the lower ½ of the spadix and characterized by their yellow-orange 22A stigmatic surfaces. An average spathe is 18–25 cm in length and 2 cm wide at the widest point.

*Seed.*—None observed to date.

Roots: Moderately thick white roots with fine laterals.

*Cold hardiness.*—Sterling has tolerated temperatures as low as 50° F. with no visible damage.

I claim:

1. A new and distinct Dieffenbachia plant as herein described and illustrated with deep shiny green leaves highlighted by a bright white midrib that extends into the leaf blade along the lateral veins and down through the petioles to the main stem.

* * * * *